United States Patent [19]

Huss, Jr. et al.

[11] Patent Number: 5,326,922

[45] Date of Patent: * Jul. 5, 1994

[54] HYDROGEN TRANSFER PROCESS

[75] Inventors: Albin Huss, Jr., Chadds Ford, Pa.; Quang N. Le, Cherry Hill; Robert T. Thomson, Lawrenceville, both of N.J.

[73] Assignee: Mobil Oil Corp., Fairfax, Va.

[*] Notice: The portion of the term of this patent subsequent to Oct. 5, 2010 has been disclaimed.

[21] Appl. No.: 929,547

[22] Filed: Aug. 13, 1992

[51] Int. Cl.$^5$ ................................................. C07C 2/58
[52] U.S. Cl. ...................................... 585/722; 585/709; 585/721
[58] Field of Search .................... 585/722, 709, 721

[56] References Cited

U.S. PATENT DOCUMENTS

| | | | |
|---|---|---|---|
| 4,439,409 | 3/1984 | Puppe et al. | 423/328 |
| 4,859,648 | 8/1989 | Landis et al. | 502/242 |
| 4,954,325 | 9/1990 | Rubin et al. | 423/328 |
| 4,992,615 | 2/1991 | Huss, Jr. et al. | 585/722 |
| 5,012,033 | 4/1991 | Child et al. | 585/722 |
| 5,073,665 | 12/1991 | Child et al. | 585/722 |
| 5,095,167 | 3/1992 | Christensen | 585/722 |

Primary Examiner—Patrick P. Garvin
Assistant Examiner—E. D. Irzinski
Attorney, Agent, or Firm—Alexander J. McKillop; Dennis P. Santini; Edward F. Kenehan, Jr.

[57] ABSTRACT

The transfer of hydrogen from a paraffin to an olefin is carried out in the presence of, as catalyst, MCM-36. Especially when the paraffin reactant is an isoparaffin, the olefin produced from the reacted isoparaffin may react with unreacted isoparaffin to also produce an alkylate product.

23 Claims, 2 Drawing Sheets

HYDROGEN TRANSFER PROCESS

CROSS-REFERENCE TO RELATED APPLICATIONS

This application is related to copending U.S. application Ser. No. 07/811,360, filed Dec. 20, 1991, now U.S. Pat. No. 5,250,277, which is a continuation-in-part of copending U.S. application Ser. No. 07/776,718, filed Oct. 15, 1991, now abandoned, which is a continuation of U.S. application Ser. No. 07/640,330, filed Jan. 11, 1991, now abandoned.

BACKGROUND

The present invention relates to a process for transferring hydrogen from a paraffin to an olefin over an MCM-36 catalyst. A particular embodiment relates to an isoparaffin-olefin alkylation and hydrogen transfer process carried out in the presence of a catalyst comprising MCM-36 to provide a product useful, inter alia, as an octane enhancer for gasoline.

As a result of the curtailment in the use of tetraethyl lead as an octane-improving additive for gasoline, not only has the production of unleaded gasoline increased but the octane number specification of all grades of gasoline have increased as well. Isoparaffin-olefin alkylation is a key route to the production of highly branched paraffin octane enhancers which are to be blended into gasolines.

Alkylation involves the addition of an alkyl group to an organic molecule. Thus, an isoparaffin can be reacted with an olefin to provide an isoparaffin of higher molecular weight. Industrially, alkylation often involves the reaction of $C_2$-$C_5$ olefins with isobutane in the presence of an acidic catalyst. Alkylates are valuable blending components for the manufacture of premium gasolines due to their high octane ratings.

In the past, alkylation processes have included the use of hydrofluoric acid or sulfuric acid as catalysts under controlled temperature conditions. Low temperatures are utilized in the sulfuric acid process to minimize the undesirable side reaction of olefin polymerization and the acid strength is generally maintained at 88-94 percent by the continuous addition of fresh acid and the continuous withdrawal of spent acid. The hydrofluoric acid process is less temperature-sensitive and the acid is easily recovered and purified.

The typical types of alkylation currently used to produce high octane gasoline blending component, that is, the hydrofluoric acid and sulfuric acid alkylation processes, have inherent drawbacks including environmental concerns, acid consumption and disposal of corrosive materials. With the increasing demands for octane and the increasing environmental concerns, it has been desirable to develop an alkylation process based on a solid catalyst system. The catalyst of the present invention offers a refiner a more environmentally acceptable alkylation process than the currently used hydrofluoric and sulfuric acid alkylation processes.

Crystalline metallosilicates, or zeolites, have been widely investigated for use in the catalysis of isoparaffin-olefin alkylation. For example, U.S. Pat. No. 3,251,902 describes the use of a fixed bed of ion-exchanged crystalline aluminosilicate having a reduced number of available acid sites for the liquid phase alkylation of $C_4$-$C_{20}$ branched-chain paraffins with $C_2$-$C_{12}$ olefins. The patent further discloses that the $C_4$-$C_{20}$ branched-chain paraffin should be allowed to substantially saturate the crystalline aluminosilicate before the olefin is introduced to the alkylation reactor.

U.S. Pat. No. 3,450,644 discloses a method for regenerating a zeolite catalyst used in hydrocarbon conversion processes involving carbonium ion intermediates.

U.S. Pat. No. 3,549,557 describes the alkylation of isobutane with $C_2$-$C_3$ olefins using certain crystalline aluminosilicate zeolite catalysts in a fixed, moving or fluidized bed system, the olefin being preferably injected at various points in the reactor.

U.S. Pat. No. 3,644,565 discloses the alkylation of a paraffin with an olefin in the presence of a catalyst comprising a Group VIII noble metal present on a crystalline aluminosilicate zeolite, the catalyst having been pretreated with hydrogen to promote selectivity.

U.S. Pat. No. 3,647,916 describes an isoparaffin-olefin alkylation process featuring the use of an ion-exchanged crystalline aluminosilicate, isoparaffin/olefin mole ratios below 3:1 and regeneration of the catalyst.

U.S. Pat. No. 3,655,813 discloses a process for alkylating $C_4$-$C_5$ isoparaffins with $C_3$-$C_9$ olefins using a crystalline aluminosilicate zeolite catalyst wherein a halide adjuvant is employed in the alkylation reactor. The isoparaffin and olefin are introduced into the alkylation reactor at specified concentrations and catalyst is continuously regenerated outside the alkylation reactor.

U.S. Pat. No. 3,893,942 describes an isoparaffin-olefin alkylation process employing, as catalyst, a Group VIII metal-containing zeolite which is periodically hydrogenated with hydrogen in the gas phase to reactivate the catalyst when it has become partially deactivated.

U.S. Pat. No. 3,236,671 discloses the use, in alkylation, of crystalline aluminosilicate zeolites having silica to alumina mole ratios above 3 and also discloses the use of various metals exchanged and/or impregnated on such zeolites.

U.S. Pat. No. 3,706,814 discloses another zeolite catalyzed isoparaffin-olefin alkylation process and further provides for the addition of $C_5+$ paraffins such as Udex raffinate or $C_5+$ olefins to the alkylation reactor feed and the use of specific reactant proportions, halide adjuvants, etc. U.S. Pat. No. 3,624,173 discloses the use, in isoparaffin-olefin alkylation, of zeolite catalysts containing gadolinium.

U.S. Pat. No. 3,738,977 discloses alkylation of paraffins with ethylene employing a zeolite catalyst which possesses a Group VIII metal component, the catalyst having been pretreated with hydrogen.

U.S. Pat. No. 3,865,894 describes the alkylation of $C_4$-$C_6$ isoparaffin with $C_3$-$C_9$ monoolefin employing a substantially anhydrous acidic zeolite, for example acidic zeolite Y (zeolite HY), and a halide adjuvant.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone after which the reactants are passed concurrently with the catalyst so that a controlled amount of olefin is adsorbed onto the catalyst before the combination of reactants and catalyst is introduced into an alkylation zone. This controlled olefin adsorption is said to prevent polymerization of the olefin during alkylation.

U.S. Pat. No. 4,377,721 describes an isoparaffin-olefin alkylation process utilizing, as catalyst, ZSM-20, preferably HZSM-20 or rare earth cation-exchanged ZSM-20.

U.S. Pat. No. 4,384,161 describes a process of alkylating isoparaffins with olefins to provide alkylate employing as catalyst a large pore zeolite capable of absorbing 2,2,4-trimethylpentane, e.g., ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large pore zeolite in combination with a Lewis acid in accordance with this patent is reported to greatly increase the activity and selectivity of the zeolite thereby effecting alkylation with high olefin space velocity and low isoparaffin/olefin ratio.

U.S. Pat. Nos. 4,992,615; 5,012,033; and 5,073,665 describe an isoparaffin-olefin alkylation process utilizing, as a catalyst, a zeolite designated as MCM-22.

SUMMARY

There is provided a process for transferring hydrogen from a paraffin to an olefin, said process comprising contacting said paraffin and said olefin under sufficient hydrogen transfer conditions, said paraffin and said olefin being contacted with a catalyst comprising MCM-36.

There is also provided a dual catalytic process for converting an isoparaffin feed and an olefin feed, said process comprising contacting both said isoparaffin feed and said olefin feed with a catalyst comprising MCM-36, wherein the reaction conditions are sufficient to cause the following two results:

(i) the transfer of hydrogen from said isoparaffin feed to said olefin feed, whereby isoparaffin feed is converted into olefin product and olefin feed is converted into a first paraffin product, said olefin product being different from said olefin feed; and (ii) said olefin product from step (i) self alkylates with unreacted isoparaffin in said isoparaffin feed to produce a second paraffin product having the number of carbon atoms equal to the sum of the carbon atoms in the olefin and isoparaffin which are reacted together in this step (ii).

Since the isoparaffin reactant in the second reaction reacts with an olefin which is produced from the same isoparaffin in the first reaction, this alkylation reaction is referred to herein as a self-alkylation reaction.

EMBODIMENTS

Figure 1:
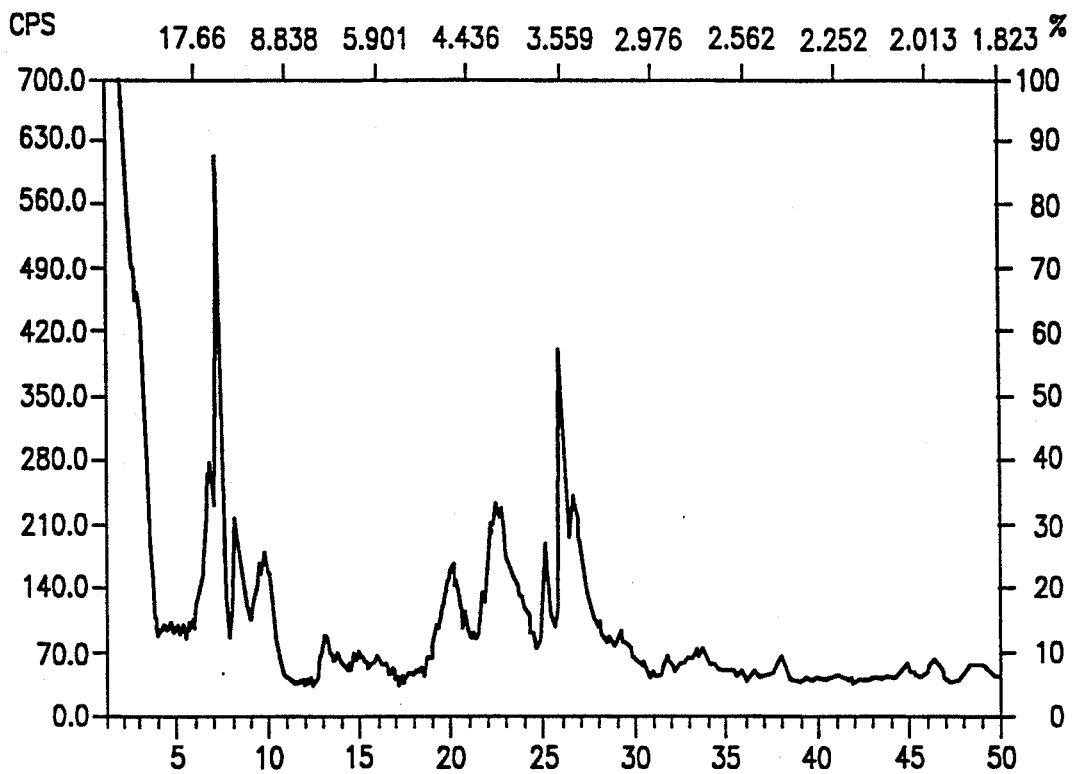
FIG. 1 is an X-ray diffraction pattern of an as-synthesized form of a layered material which may be swollen and pillared.

Isoparaffin-light olefin alkylation plays an important role in the manufacture of high octane gasoline blending stocks with alkylate typically comprising 10-15% of the gasoline pool. Alkylate is an especially valuable component of the gasoline pool as it possesses both high research and motor octane (low sensitivity) numbers, contains no olefins or aromatics and little or no sulfur, demonstrates excellent stability and is clean burning. One measure of the selectivity of an alkylation catalyst is the $C_9+$ yield. This fraction generally results from oligomerization of the feed olefins resulting in a loss of alkylate yield, reduced alkylate quality and the possible formation of an acidic sludge fraction.

The product produced by the process of this invention may be of high quality based on both research and motor octane numbers and as such may be particularly well suited for blending into the gasoline pool.

MCM-36 and methods for its preparation are described in the aforementioned U.S. application Ser. No. 07/811,360, filed Dec. 20, 1991, the entire disclosure of which is expressly incorporated herein by reference.

MCM-36 may be prepared from an intermediate material which is crystallized in the presence of a hexamethyleneimine directing agent and which, if calcined, without being swollen would be transformed into a material having an X-ray diffraction pattern as shown in Table 1.

TABLE 1

| Interplanar d-Spacing (A) | Relative Intensity, $I/I_o \times 100$ |
|---|---|
| 30.0 ± 2.2 | w-m |
| 22.1 ± 1.3 | w |
| 12.36 ± 0.2 | m-vs |
| 11.03 ± 0.2 | m-s |
| 8.83 ± 0.14 | m-vs |
| 6.86 ± 0.14 | w-m |
| 6.18 ± 0.12 | m-vs |
| 6.00 ± 0.10 | w-m |
| 5.54 ± 0.10 | w-m |
| 4.92 ± 0.09 | w |
| 4.64 ± 0.08 | w |
| 4.41 ± 0.08 | w-m |
| 4.25 ± 0.08 | w |
| 4.10 ± 0.07 | w-s |
| 4.06 ± 0.07 | w-s |
| 3.91 ± 0.07 | m-vs |
| 3.75 ± 0.06 | w-m |
| 3.56 ± 0.06 | w-m |
| 3.42 ± 0.06 | vs |
| 3.30 ± 0.05 | w-m |
| 3.20 ± 0.05 | w-m |
| 3.14 ± 0.05 | w-m |
| 3.07 ± 0.05 | w |
| 2.99 ± 0.05 | w |
| 2.82 ± 0.05 | w |
| 2.78 ± 0.05 | w |
| 2.68 ± 0.05 | w |
| 2.59 ± 0.05 | w |

The values in this Table and like tables presented hereinafter were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Tables 1–8, the relative intensities are given in terms of the symbols w=weak, m=medium, s=strong and vs=very strong. In terms of intensities, these may be generally designated as follows:

w=0-20
m=20-40
s=40-60
vs=60-100

The material having the X-ray diffraction pattern of Table 1 is known as MCM-22 and is described in U.S. Pat. No. 4,954,325, the entire disclosure of which is incorporated herein by reference. This material can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10-80 | 10-60 |
| $H_2O/YO_2$ | 5-100 | 10-50 |
| $OH^-/YO_2$ | 0.01-1.0 | 0.1-0.5 |
| $M/YO_2$ | 0.01-2.0 | 0.1-1.0 |
| $R/YO_2$ | 0.05-1.0 | 0.1-0.5 |

In the synthesis method for preparing the material having the X-ray diffraction pattern of Table 1, the source of $YO_2$ must be comprised predominately of solid $YO_2$, for example at least about 30 wt. % solid $YO_2$ in order to obtain the desired crystal product. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free H20 and about 4.5 wt. % bound H20 of hydration and having a particle size of about 0.02 micron) favors crystal formation from the above mixture and is a distinct improvement over the synthesis method taught in U.S. Pat. No. 4,439,409. If another source of oxide of silicon e.g., Q-Brand (a sodium silicate comprised of about 28.8 wt. % $SiO_2$, 8.9 wt. % $Na_2O$ and 62.3 wt. % $H_2O$) is used, crystallization yields little or none of the crystalline material having the X-ray diffraction pattern of Table 1. Impurity phases of other crystal structures, e.g., ZSM-12, are prepared in the latter circumstance. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the crystalline material having the X-ray diffraction pattern of Table 1 can be carried out at either static or stirred conditions in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g., from about 24 hours to about 60 days. Thereafter, the crystals are separated from the liquid and recovered.

The organic directing agent for use in synthesizing the present crystalline material from the above reaction mixture may be hexamethyleneimine which has the following structural formula:

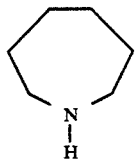

Other organic directing agents which may be used include 1,4-diazacycloheptane, azacyclooctane, aminocyclohexane, aminocycloheptane, aminocyclopentane, N,N,N-trimethyl-1-adamantanammonium ions, and N,N,N-trimethyl-2-adamantanammonium ions. In general, the organic directing agent may be selected from the group consisting of heterocyclic imines, cycloalkyl amines and adamantane quaternary ammonium ions.

It should be realized that the reaction mixture components can be supplied by more than one source. The reaction mixture can be prepared either batchwise or continuously. Crystal size and crystallization time of the crystalline material will vary with the nature of the reaction mixture employed and the crystallization conditions.

Synthesis of crystals may be facilitated by the presence of at least 0.01 percent, e.g., 0.10 percent or 1 percent, seed crystals (based on total weight) of crystalline product.

The crystalline material having the X-ray diffraction pattern of Table 1 passes through an intermediate stage. The material at this intermediate stage has a different X-ray diffraction pattern than that set forth in Table 1. It has further been discovered that this intermediate material is swellable with the use of suitable swelling agents such as cetyltrimethylammonium compounds, e.g., cetyltrimethylammonium hydroxide. However, when this swollen intermediate material is calcined, even under mild conditions, whereby the swelling agent is removed, the material can no longer be swollen with such swelling agent. By way of contrast it is noted that various layered silicates such as magadiite and kenyaite may be swellable with cetyltrimethylammonium compounds both prior to and after mild calcination.

The present swollen products may have relatively high interplanar distance (d-spacing), e.g., greater than about 6 Angstrom, e.g., greater than about 10 Angstrom and even exceeding 30 Angstrom. These swollen materials may be converted into pillared materials. These pillared materials, particularly silica pillared materials, may be capable of being exposed to severe conditions such as those encountered in calcining, e.g., at temperatures of about 450° C. for about two or more hours, e.g., four hours, in nitrogen or air, without significant decrease, e.g., less than about 10%, in interlayer distance.

The material having the X-ray diffraction pattern of Table 1, when intercepted in the swellable, intermediate state, prior to final calcination, may have the X-ray diffraction pattern shown in Table 2.

TABLE 2

| d(A) | $I/I_o$ |
|---|---|
| 13.53 ± 0.2 | m-vs |
| 12.38 ± 0.2 | m-vs |
| 11.13 ± 0.2 | w-s |
| 9.15 ± 0.15 | w-s |
| 6.89 ± 0.15 | w-m |
| 4.47 ± 0.10 | w-m |
| 3.95 ± 0.08 | w-vs |
| 3.56 ± 0.06 | w-m |
| 3.43 ± 0.06 | m-vs |
| 3.36 ± 0.05 | w-s |

An X-ray diffraction pattern trace for an example of such an as-synthesized, swellable material is shown in FIG. 1. A particular example of such an as-synthesized, swellable material is the material of Example 1 of the aforementioned U.S. Pat. No. 4,954,325. This material of Example 1 of U.S. Pat. No. 4,954,325 has the X-ray diffraction pattern given in the following Table 3.

TABLE 3

| 2 Theta | d(A) | I/I$_o$ × 100 |
|---|---|---|
| 3.1 | 28.5 | 14 |
| 3.9 | 22.7 | <1 |
| 6.53 | 13.53 | 36 |
| 7.14 | 12.38 | 100 |
| 7.94 | 11.13 | 34 |
| 9.67 | 9.15 | 20 |
| 12.85 | 6.89 | 6 |
| 13.26 | 6.68 | 4 |
| 14.36 | 6.17 | 2 |
| 14.70 | 6.03 | 5 |
| 15.85 | 5.59 | 4 |
| 19.00 | 4.67 | 2 |
| 19.85 | 4.47 | 22 |
| 21.56 | 4.12 | 10 |
| 21.94 | 4.05 | 19 |
| 22.53 | 3.95 | 21 |
| 23.59 | 3.77 | 13 |
| 24.98 | 3.56 | 20 |
| 25.98 | 3.43 | 55 |
| 26.56 | 3.36 | 23 |
| 29.15 | 3.06 | 4 |
| 31.58 | 2.833 | 3 |
| 32.34 | 2.768 | 2 |
| 33.48 | 2.676 | 5 |
| 34.87 | 2.573 | 1 |
| 36.34 | 2.472 | 2 |
| 37.18 | 2.418 | 1 |
| 37.82 | 2.379 | 5 |

Taking into account certain modifications, this swellable material may be swollen and pillared by methods generally discussed in the aforementioned U.S. Pat. No. 4,859,648, the entire disclosure of which is expressly incorporated herein be reference. The present modifications are discussed hereinafter and include the selection of proper swelling pH and swelling agent.

Upon being swollen with a suitable swelling agent, such as a cetyltrimetylammonium compound, the swollen material may have the X-ray diffraction pattern shown in Table 4.

TABLE 4

| d(A) | I/I$_o$ |
|---|---|
| >32.2 | vs |
| 12.41 ± 0.25 | w-s |
| 3.44 ± 0.07 | w-s |

The X-ray diffraction pattern of this swollen material may have additional lines with a d(A) spacing less than the line at 12.41±0.25, but none of said additional lines have an intensity greater than the line at the d(A) spacing of 12.41±0.25 or at 3.44±0.07, whichever is more intense. More particularly, the X-ray diffraction pattern of this swollen material may have the lines shown in the following Table 5.

TABLE 5

| d(A) | I/I$_o$ |
|---|---|
| >32.2 | vs |
| 12.41 ± 0.25 | w-s |
| 11.04 ± 0.22 | w |
| 9.28 ± 0.19 | w |
| 6.92 ± 0.14 | w |
| 4.48 ± 0.09 | w-m |
| 3.96 ± 0.08 | w-m |
| 3.57 ± 0.07 | w-m |
| 3.44 ± 0.07 | w-s |
| 3.35 ± 0.07 | w |

Even further lines may be revealed upon better resolution of the X-ray diffraction pattern. For example, the X-ray diffraction pattern may have additional lines at the following d(A) spacings (intensities given in parentheses): 16.7±4.0 (w-m); 6.11±0.24 (w); 4.05±0.08 (w); and 3.80±0.08 (w).

In the region with d<9 A, the pattern for the swollen material is essentially like the one given in Table 2 for the unswollen material, but with the possibility of broadening of peaks.

Figure 2:
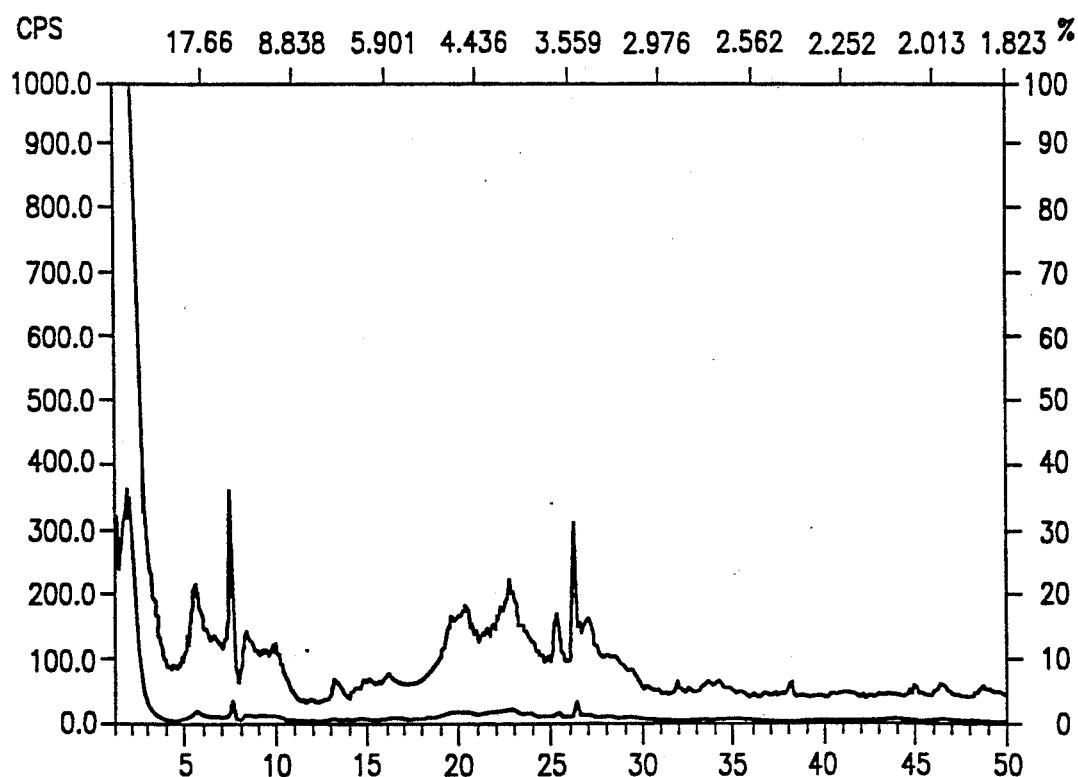
FIG. 2 is an X-ray diffraction pattern of a swollen form of the material having the X-ray diffraction pattern shown in FIG. 1.

An X-ray diffraction pattern trace for an example of such a swollen material is shown in FIG. 2. The upper profile is a 10-fold magnification of the lower profile in FIG. 2.

Upon being pillared with a suitable polymeric oxide, such as polymeric silica, the swollen material having the X-ray diffraction pattern shown in Table 4 may be converted into a material having the X-ray diffraction pattern shown in Table 6.

TABLE 6

| d(A) | I/I$_o$ |
|---|---|
| >32.2 | vs |
| 12.38 ± 0.25 | w-m |
| 3.42 ± 0.07 | w-m |

The x-ray diffraction pattern of this pillared material may have additional lines with a d(A) spacing less than the line at 12.38±0.25, but none of said additional lines have an intensity greater than the line at the d(A) spacing of 12.38±0.25 or 3.42±0.07, whichever is more intense. More particularly, the X-ray diffraction pattern of this pillared material may have the lines shown in the following Table 7.

TABLE 7

| d(A) | I/I$_o$ |
|---|---|
| >32.2 | vs |
| 12.38 ± 0.25 | w-m |
| 10.94 ± 0.22 | w-m |
| 9.01 ± 0.18 | w |
| 6.88 ± 0.14 | w |
| 6.16 ± 0.12 | w-m |
| 3.93 ± 0.08 | w-m |
| 3.55 ± 0.07 | w |
| 3.42 ± 0.07 | w-m |
| 3.33 ± 0.07 | w-m |

Even further lines may be revealed upon better resolution of the X-ray diffraction pattern. For example, the X-ray diffraction pattern may have additional lines at the following d(A) spacings (intensities given in parentheses): 5.59±0.11 (w); 4.42±0.09 (w); 4.11±0.08 (w); 4.04±0.08 (w); and 3.76±0.08 (w).

Figure 3:
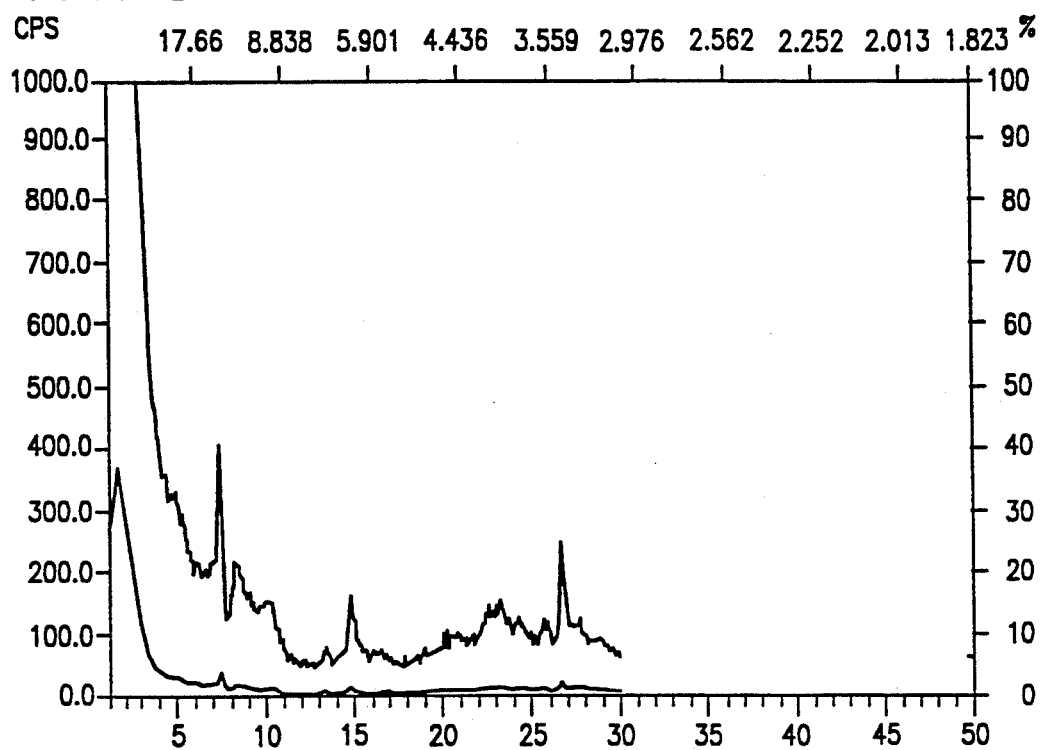
FIG. 3 is an X-ray diffraction pattern of the pillared form of the layered material having the X-ray diffraction pattern shown in FIG. 1.

An X-ray diffraction pattern trace for an example of such a pillared material is given in FIG. 3. The upper profile is a 10-fold magnification of the lower profile in FIG. 3.

If the material swollen with a suitable swelling agent is calcined without prior pillaring another material is produced. For example, if the material which is swollen but not pillared is calcined in air for 6 hours at 540° C., a very strong line at a d(A) spacing of greater than 32.2 will no longer be observed. By way of contrast, when the swollen, pillared material is calcined in air for 6 hours at 540° C., a very strong line at a d(A) spacing of greater than 32.2 will still be observed, although the precise position of the line may shift.

An example of a swollen, non-pillared material, which has been calcined, has the pattern as shown in Table 8.

TABLE 8

| 2 Theta | d(A) | I/I$_o$ × 100 | |
|---|---|---|---|
| 3.8 | 23.3 | 12 | |
| 7.02 | 12.59 | 100 | |
| 8.02 | 11.02 | 20 | |
| 9.66 | 9.16 | 14 | |
| 12.77 | 6.93 | 7 | |
| 14.34 | 6.18 | 45 | |
| 15.75 | 5.63 | 8 | |
| 18.19 | 4.88 | 3 | |
| 18.94 | 4.69 | 3 | |
| 19.92 | 4.46 | 13 | broad |
| 21.52 | 4.13 | 13 | shoulder |
| 21.94 | 4.05 | 18 | |
| 22.55 | 3.94 | 32 | |
| 23.58 | 3.77 | 16 | |
| 24.99 | 3.56 | 20 | |
| 25.94 | 3.43 | 61 | |
| 26.73 | 3.33 | 19 | |
| 31.60 | 2.831 | 3 | |
| 33.41 | 2.682 | 4 | |
| 34.62 | 2.591 | 3 | broad |
| 36.36 | 2.471 | 1 | |
| 37.81 | 2.379 | 4 | |

The X-ray powder pattern shown in Table 8 is similar to that shown in Table 1 except that most of the peaks in Table 8 are much broader than those in Table 1.

Figure 4:
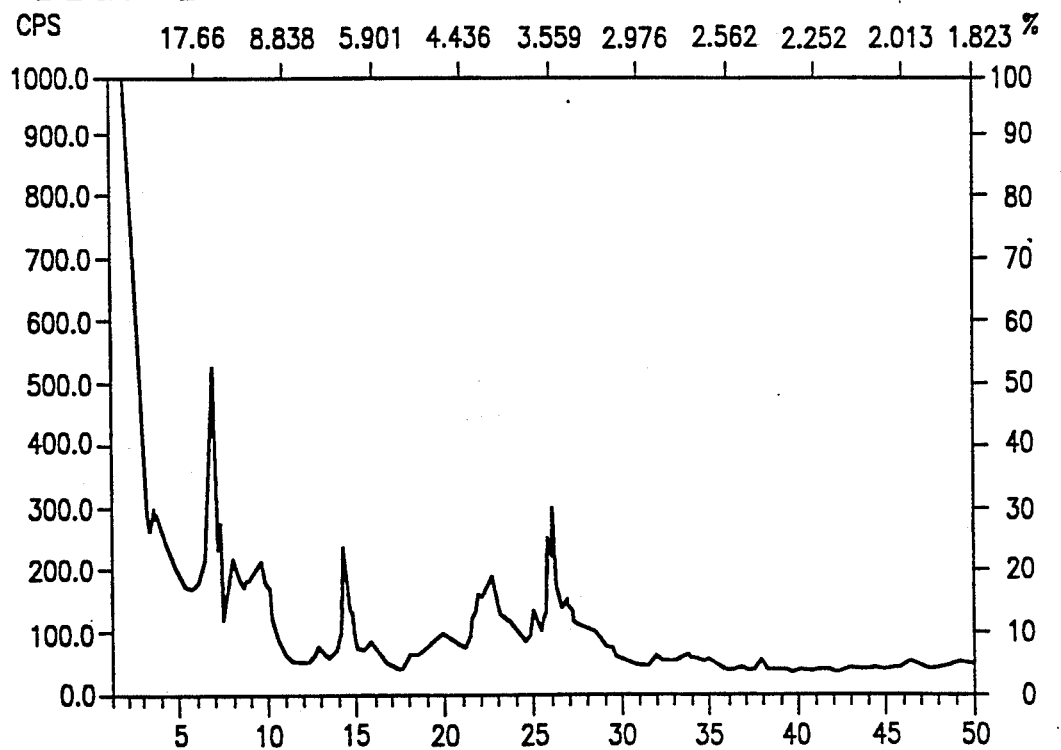
FIG. 4 is an X-ray diffraction pattern of the calcined form of the swollen material having the X-ray diffraction pattern shown in FIG. 2.

An X-ray diffraction pattern trace for an example of the calcined material corresponding to Table 8 is given in FIG. 4.

As mentioned previously, the calcined material corresponding to the X-ray diffraction pattern of Table 1 is designated MCM-22. For the purposes of the present disclosure, the pillared material corresponding to the X-ray diffraction pattern of Table 6 is designated herein as MCM-36. The swollen material corresponding to the X-ray diffraction pattern of Table 4 is designated herein as the swollen MCM-22 precursor. The as-synthesized material corresponding to the X-ray diffraction pattern of Table 2 is referred to herein, simply, as the MCM-22 precursor.

The layers of the swollen material of this disclosure may have a composition involving the molar relationship:

X$_2$O$_3$:(n)YO$_2$, wherein X is a trivalent element, such as aluminum, boron, iron and/or gallium, preferably aluminum, Y is a tetravalent element such as silicon and/or germanium, preferably silicon, and n is at least about 5, usually from about 10 to about 150, more usually from about 10 to about 60, and even more usually from about 10 to about 40.

To the extent that the layers of the swollen MCM-22 precursor and MCM-36 have negative charges, these negative charges are balanced with cations. For example, expressed in terms of moles of oxides, the layers of the swollen MCM-22 precursor and MCM-36 may have a ratio of 0.5 to 1.5 R$_2$O:X$_2$O$_3$, where R is a monovalent cation or 1/m of a cation of valency m.

MCM-36 adsorbs significant amounts of commonly used test adsorbate materials, i.e., cyclohexane, n-hexane and water. Adsorption capacities for this pillared material, especially the silica pillared material, may range at room temperature as follows:

| Adsorbate | Capacity, Wt. Percent |
|---|---|
| n-hexane | 17–40 |
| cyclohexane | 17–40 |
| water | 10–40 | wherein cyclohexane and n-hexane sorption are measured at 20 Torr and water sorption is measured at 12 Torr.

The swellable material, used to form the swollen material of the present disclosure, may be initially treated with a swelling agent. Such swelling agents are materials which cause the swellable layers to separate by becoming incorporated into the interspathic region of these layers. The swelling agents are removable by calcination, preferably in an oxidizing atmosphere, whereby the swelling agent becomes decomposed and/or oxidized.

Suitable swelling agents may comprise a source of organic cation, such as quaternary organoammonium or organophosphonium cations, in order to effect an exchange of interspathic cations. Organoammonium cations, such as n-octylammonium, showed smaller swelling efficiency than, for example, cetyltrimethylammonium. A pH range of 11 to 14, preferably 12.5 to 13.5 is generally employed during treatment with the swelling agent.

The as-synthesized material is preferably not dried prior to being swollen. This as-synthesized material may be in the form of a wet cake having a solids content of less than 30 % by weight, e.g., 25 wt % or less.

The foregoing swelling treatment results in the formation of a layered oxide of enhanced interlayer separation depending upon the size of the organic cation introduced. In one embodiment, a series of organic cation exchanges can be carried out. For example, an organic cation may be exchanged with an organic cation of greater size, thus increasing the interlayer separation in a step-wise fashion. When contact of the layered oxide with the swelling agent is conducted in aqueous medium, water is trapped between the layers of the swollen species.

The organic-swollen species may be treated with a compound capable of conversion, e.g., by hydrolysis and/or calcination, to pillars of an oxide, preferably to a polymeric oxide. Where the treatment involves hydrolysis, this treatment may be carried out using the water already present in organic-swollen material. In this case, the extent of hydrolysis may be modified by varying the extent to which the organic-swollen species is dried prior to addition of the polymeric oxide precursor.

It is preferred that the organic cation deposited between the layers be capable of being removed from the pillared material without substantial disturbance or removal of the interspathic polymeric oxide. For example, organic cations such as cetyltrimethylammonium may be removed by exposure to elevated temperatures, e.g., calcination, in nitrogen or air, or by chemical oxidation preferably after the interspathic polymeric oxide precursor has been converted to the polymeric oxide pillars in order to form the pillared layered product.

These pillared layered products, especially when calcined, exhibit high surface area, e.g., greater than 500 m$^2$/g, and thermal and hydrothermal stability making them highly useful as catalysts or catalytic supports, for hydrocarbon conversion processes, for example, alkylation.

Insertion of the organic cation between the adjoining layers serves to physically separate the layers in such a way as to make the layered material receptive to the interlayer addition of a polymeric oxide precursor. In particular, cetyltrimethylammonium cations have been found useful. These cations are readily incorporated within the interlayer spaces of the layered oxide serving to prop open the layers in such a way as to allow incorporation of the polymeric oxide precursor. The extent of the interlayer spacing can be controlled by the size of the organoammonium ion employed.

Interspathic oxide pillars, which may be formed between the layers of the propped or swollen oxide material, may include an oxide, preferably a polymeric oxide, of zirconium or titanium or more preferably of an element selected from Group IVB of the Periodic Table (Fischer Scientific Company Cat. No. 5-702-10, 1978), other than carbon, i.e., silicon, germanium, tin and lead. Other suitable oxides include those of Group VA, e.g., V, Nb, and Ta, those of Group IIA, e.g., Mg or those of Group IIIB, e.g., B. Most preferably, the pillars include polymeric silica. In addition, the oxide pillars may include an element which provides catalytically active acid sites in the pillars, preferably aluminum.

The oxide pillars are formed from a precursor material which may be introduced between the layers of the organic "propped" species as an ionic or electrically neutral compound of the desired elements, e.g., those of Group IVB. The precursor material may be an organometallic compound which is a liquid under ambient conditions. In particular, hydrolyzable compounds, e.g., alkoxides, of the desired elements of the pillars may be utilized as the precursors. Suitable polymeric silica precursor materials include tetraalkylsilicates, e.g., tetrapropyl-orthosilicate, tetramethylorthosilicate and, most preferably, tetraethylorthosilicate. Suitable polymeric silica precursor materials also include quaternary ammonium silicates, e.g., tetramethylammonium silicate (i.e. TMA silicate). Where the pillars also include polymeric alumina, a hydrolyzable aluminum compound can be contacted with the organic "propped" species before, after or simultaneously with the contacting of the propped layered oxide with the silicon compound. Preferably, the hydrolyzable aluminum compound employed is an aluminum alkoxide, e.g., aluminum isopropoxide. If the pillars are to include titania, a hydrolyzable titanium compound such as titanium alkoxide, e.g., titanium isopropoxide, may be used.

After calcination to remove the organic propping agent, the final pillared product may contain residual exchangeable cations. Such residual cations in the layered material can be ion exchanged by known methods with other cationic species to provide or alter the catalytic activity of the pillared product. Suitable replacement cations include cesium, cerium, cobalt, nickel, copper, zinc, manganese, platinum, lanthanum, aluminum, ammonium, hydronium and mixtures thereof.

Particular procedures for intercalating layered materials with metal oxide pillars are described in U.S. Pat. Nos. 4,831,005; 4,831,006; and 4,929,587. The entire disclosures of these patents are expressly incorporated herein by reference. U.S. Pat. No. 4,831,005 describes plural treatments with the pillar precursor. U.S. Pat. No. 4,929,587 describes the use of an inert atmosphere, such as nitrogen, to minimize the formation of extralaminar polymeric oxide during the contact with the pillar precursor. U.S. Pat. No. 4,831,006 describes the use of elevated temperatures during the formation of the pillar precursor.

The resulting pillared products exhibit thermal stability at temperatures of 450° C. or even higher as well as substantial sorption capacities (as much as 17 to 40 wt. % for $C_6$ hydrocarbon). The pillared products may possess a basal spacing of at least about 32.2A and surface areas greater than 500 $m^2/g$.

The layered material may be subjected to thermal treatment, e.g., to decompose organoammonium ions. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience.

Prior to its use as a catalyst, MCM-36 should be subjected to thermal treatment to remove part or all of any organic constituent present therein.

MCM-36 can optionally be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. MCM-36 can also optionally be used in intimate combination with a rare earth component such as lanthanum or cerium. Such component can be associated chemically and/or physically with the MCM-36 and/or matrix with which the MCM-36 may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the MCM-36 such as, for example, by, in the case of platinum, treating the MCM-36 with a solution containing the platinum metal-containing ion. Thus, suitable platinum compounds for this purpose include chloroplatinic acid, platinous chloride and various compounds containing the platinum amine complex.

The MCM-36, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use as a catalyst, the MCM-36 crystals may be at least partially dehydrated. This dehydration can be accomplished by heating the MCM-36 to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the MCM-36 in a vacuum but a longer time will be required to achieve a suitable degree of dehydration.

The MCM-36 can be shaped into a wide variety of particle sizes. Generally speaking, the particles can be provided in the form of a powder, a granule or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desired to incorporate the MCM-36 with another material, i.e., a binder, which is resistant to the temperatures and other conditions employed in the isoparaffin alkylation process of this invention. Suitable binder materials include active and inactive materials and synthetic or naturally occurring zeolites as well as inorganic materials such as clays, silica and/or metal oxides such as alumina. The latter can be either naturally occurring or provided in the form of gelatinous precipitates or gels including mixtures of silica and metal oxides. Use of a binder material in conjunction with MCM-36, i.e., combined therewith or present during its synthesis, which itself is catalytically active may change the conversion and/or selectivity of the catalyst. Inactive materials suitably serve as diluents to control the amount of conversion so that products can be obtained economically and in a controlled fashion without having to employ other means for controlling the rate of reaction. These materials can be incorporated into naturally occurring clays, e.g., bentonite and kaolin, to improve the crush strength of the MCM-36 under commercial operating conditions. Good crush strength is an advantageous attribute for commercial use since it prevents or delays breaking down of the catalyst into powder-like materials.

Naturally occurring clays which can be composited with MCM-36 crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with MCM-36 also include inorganic oxides, notably alumina.

Apart from or in addition to the foregoing binder materials, the MCM-36 crystals can be composited with an inorganic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may be advantageous to provide at least a part of the foregoing matrix materials in colloidal form so as to facilitate extrusion of the bound catalyst component(s).

The relative proportions of finely divided MCM-36 and inorganic oxide matrix can vary widely with the MCM-36 content ranging from about 1 to about 95 percent by weight and more usually, particularly when the composite is prepared in the form of beads, in the range of about 2 to about 80 weight percent of the composite.

The operating temperature of the hydrogen transfer or the dual hydrogen transfer/alkylation process described herein can extend over a fairly broad range, e.g., from about $-25°$ to about 400° C., and is preferably within the range of from about 75° C. to about 200° C. The practical upper operating temperature will often be dictated by the need to avoid an undue occurrence of undesirable side reactions.

The pressures employed in the present process can extend over a considerably wide range, e.g., from subatmospheric pressure to about 5000 psig, and preferably from atmospheric pressure to about 2000 psig.

The amount of MCM-36 used in the present hydrogen transfer or dual hydrogen transfer/alkylation process can be varied over relatively wide limits. In general, the amount of MCM-36 as measured by the weight hourly space velocity (WHSV) based on olefin can range from about 0.01 to about 100 hr$^{-1}$, preferably from 0.05 to 5 hr$^{-1}$. It will, of course, be realized by those skilled in the art that the amount of catalyst selected for a particular reaction will be determined by several variables including the reactants involved as well as the nature of the catalyst and the operating conditions employed.

The paraffin feed may comprise one or more paraffins, especially isoparaffins. The paraffin or isoparaffin reactant used in the present alkylation process may be one possessing up to about 20 carbon atoms and preferably one having from about 4 to about 8 carbon atoms as, for example, isobutane, 3-methylhexane, 2-methylbutane, 2,3-dimethylbutane and 2,4-dimethylhexane.

The olefin feed may comprise one or more olefins, especially branched olefins. The olefin reactant employed herein generally contains from 2 to about 12 carbon atoms. Representative examples are ethylene, propylene, butene-1, butene-2, isobutylene, pentenes, hexenes, heptenes and octenes. Particular olefin feeds may comprise one or more olefins having from 5 to 8, e.g. 6 to 8, carbon atoms.

Olefinic feedstocks suitable for use in the present invention include numerous olefinic streams produced by petroleum refining operations, for example, a cracking operation. In a particular cracking operation, a cracked olefinic stream such as an olefinic gasoline boiling range fraction is produced from a delayed coker process unit. Delayed coking processes are taught in U.S. Pat. No. 3,917,564 to Meyers and U.S. Pat. No. 4,874,505 to Bartilucci et al., both of which patents are incorporated herein by reference.

Suitable olefinic feedstocks are also produced as by-products in catalytic dewaxing processes. An example of such a process is described in U.S. Pat. No. 4,922,048, which patent is incorporated herein by reference.

Suitable olefinic feedstocks may also be produced during oligomerization processes, such as MOGD and MOGDL, which are described more fully hereinafter.

Recent developments in zeolite catalysts and hydrocarbon conversion methods and apparatuses have created interest in utilizing olefinic feedstocks for producing heavier hydrocarbons, such as C$_5$+ gasoline, distillate or lubes. These developments form the basis of the Mobil olefins to gasoline/distillate (MOGD) method and apparatus, and the Mobil olefins to gasoline/distillate/lubes (MOGDL) method and apparatus.

In MOGD and MOGDL, olefins are catalytically converted to heavier hydrocarbons by catalytic oligomerization using an acid crystalline zeolite, such as a zeolite catalyst having the structure of ZSM-5. Process conditions can be varied to favor the formation of either gasoline, distillate or lube range products. U.S. Pat. Nos. 3,960,978 and 4,021,502 to Plank et al. the conversion of C$_2$-C$_5$ olefins alone or in combination with paraffinic components, into higher hydrocarbons over a crystalline zeolite catalyst. U.S. Pat. Nos. 4,150,062; 4,211,640 and 4,227,992 to Garwood et al. have contributed improved processing techniques to the MOGD system. U.S. Pat. No. 4,456,781 to Marsh et al. has also disclosed improved processing techniques for the MOGD system.

Olefinic feedstocks may be obtained from various sources, including from fossil fuel processing streams such as gas separation units, from the cracking of $C_2$-hydrocarbons, such as LPG (liquified petroleum gas) from coal by-products, from various synthetic fuel processing streams, and as by-products from fluid catalytic cracking (FCC) and thermal catalytic cracking (TCC) process units. U.S. Pat. No 4,100,218 to Chen et al. teaches thermal cracking of ethane to ethylene, with subsequent conversion of ethylene to LPG and gasoline over a zeolite catalyst having the structure of ZSM-5.

In general, the mole ratio of total paraffin or isoparaffin to total olefin in the combined hydrocarbon feed can be from about 1:2 to about 500:1 and is preferably in the range of from about 5:1 to about 50:1. The paraffin, isoparaffin and/or olefin reactants can be in either the vapor phase or the liquid phase and can be neat, i.e., free from intentional admixture of dilution with other material, or the reactants can be brought into contact with the catalyst composition with the aid of carrier gases or diluents such as, for example, hydrogen or nitrogen. The reactants also may optionally be introduced to the reaction zone together with one or more other reactive materials which serve to enhance the overall conversion operation.

The process of the present invention can be carried out as a batch-type, semi-continuous or continuous operation utilizing a fixed or moving bed of the MCM-36 catalyst component. A preferred embodiment entails use of a catalyst zone wherein the hydrocarbon charge is passed concurrently or countercurrently through a moving bed of particle-form MCM-36 catalyst. The latter, after use, is conducted to a regeneration zone where coke is removed, e.g., by burning in an oxygen-containing atmosphere (such as air) at elevated temperature or by extracting with a solvent, after which the regenerated catalyst is recycled to the conversion zone for further contact with the organic reactants.

In order to more fully illustrate the process of this invention and the manner of practicing same, the following examples are presented. In examples illustrative of the synthesis of MCM-36, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the absorbent, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant.

EXAMPLE 1

A combination of 504 g of water, 11.4 g of 50% sodium hydroxide, 11.4 g of sodium aluminate (43.5% $Al_2O_3$, 30% $Na_2O$), 64.9 g of silica (Ultrasil) and 34.2 g of hexamethyleneimine was reacted in an autoclave at 143° C. for 48 hours with stirring. The product was filtered and washed thoroughly with water.

500 g of the wet cake material (24% solids) described above was mixed with 3 l of 29% CTMA-OH (cetyltrimethylammonium hydroxide—pH=13.5, obtained by anion exchange of 29% CTMA-Cl with 0.9 l of IRA-400(OH) from ALPHA) and stirred for 48 hours at room temperature. The swollen product was isolated by filtration, washed twice with 500 ml of water and air dried overnight. The X-ray diffraction pattern for this swollen material is given in the following Table 9.

TABLE 9

| 2 Theta | d(A) | $I/I_o \times 100$ | |
|---|---|---|---|
| 1.7 | 52.0 | 100 | |
| 5.18 | 17.06 | 7.3 | |
| 6.81 | 12.98 | 2.3 | |
| 7.10 | 12.45 | 5.7 | |
| 8.79 | 10.06 | 2.7 | very broad |
| 12.73 | 6.95 | 0.6 | |
| 13.82 | 6.41 | 0.4 | |
| 14.55 | 6.09 | 0.3 | |
| 15.59 | 5.68 | 0.7 | |
| 18.39 | 4.82 | 1.3 | broad shoulder |
| 19.06 | 4.66 | 2.6 | shoulder |
| 19.77 | 4.49 | 4.8 | |
| 21.01 | 4.23 | 3.4 | broad |
| 22.28 | 3.99 | 5.0 | |
| 23.35 | 3.81 | 2.3 | broad shoulder |
| 24.91 | 3.57 | 3.0 | |
| 25.90 | 3.44 | 8.0 | |
| 26.50 | 3.36 | 4.4 | |

235 g of this swollen material was ground and combined with 1.4 liter of TEOS (tetraethylorthosilicate). The TEOS treated material was heated under a stream of nitrogen. After filtration and drying the product was hydrolyzed in water. The pillared product contained 65% solids based on calcination at 540° C.

The X-ray diffraction pattern for this pillared, calcined material is given in the following Table 10.

TABLE 10

| 2 Theta | d(A) | $I/I_o \times 100$ | |
|---|---|---|---|
| 1.7 | 52.0 | 100 | |
| 7.13 | 12.40 | 23.3 | |
| 8.08 | 10.94 | 7.3 | broad |
| 12.84 | 6.89 | 1.5 | |
| 14.38 | 6.16 | 8.4 | |
| 15.83 | 5.60 | 0.9 | |
| 19.88 | 4.47 | 2.3 | broad |
| 21.61 | 4.11 | 2.2 | |
| 22.07 | 4.03 | 3.3 | broad |
| 22.67 | 3.92 | 4.3 | broad |
| 23.67 | 3.76 | 2.7 | |
| 25.06 | 3.55 | 4.0 | |
| 26.06 | 3.42 | 12.8 | |
| 26.75 | 3.33 | 4.1 | |

EXAMPLE 2

An alumina-bound MCM-36 catalyst was prepared by mulling and then extruding (1/16" extrudate) a 65/35 (wt./wt.) mixture of MCM-36 (prepared as described in above Example 1) and Versal 250 alumina. The extrudate product was then dried at 250° F. overnight. After drying, the MCM-36 extrudate was calcined by the following method: 3 hr in nitrogen at 450° C. followed by slow bleeding of air and full air calcination at 540° C. for hours. Following calcination, the extrudate was exchanged with 1 N NH₄NO₃, washed with deionized water, recalcined at 540° C. for hours and finally crushed and sized to 30/60 mesh for catalytic evaluation.

EXAMPLE 3

A sufficient amount of the extruded catalyst of Example 2 to provide 5.0 g of MCM-36 was crushed and added to a 300 cc autoclave. Following a successful pressure test, 90 g of isobutane and 13 g of 2,3-dimethyl-2-butene were charged to the reactor and the stirring rate increased to 500 RPM. The pressure of the autoclave was increased to 150 psig by adding nitrogen, and the temperature increased to 300° F. at a rate of 5° F./min. Reactor pressure reached 700 psig after the maximum temperature was reached. A sample of the hydrocarbon was taken 24 hours after the commencement of heating. Analysis of the reaction products was performed using a gas chromatograph equipped with a silica capillary column. Results are given in Table 11. In Table 11, HC stands for hydrocarbon, IC₄ stands for isobutane, C₆= stands for 2,3-dimethyl-2-butene, TMP stands for trimethylpentane and DMH stands for dimethylhexane.

TABLE 11

| Production of C₈ Isoparaffins During Isobutane/C₆= Reactions | |
|---|---|
| Temp., °F. | 300 |
| Pressure, psig | 700 |
| HC/MCM-36, w/w | 20 |
| Initial IC₄/C₆=, mole ratio | 10 |
| Hours on Stream | 24 |
| Olefin conv., Wt % | 97 |
| C₅+ HC Dist., Wt % | |
| C₅ | 8 |
| C₆ | 23 |
| C₇ | 8 |
| C₈ | 24 |
| C₉+ | 38 |
| Normalized C₈ Dist., Wt % | |
| 2,2,4 TMP | 50 |
| 2,3,4 TMP | 12 |
| 2,3,3 TMP | 13 |
| 2,5 DMH | 9 |
| 2,4 DMH | 7 |
| 2,3 DMH | 6 |
| 3,4 DMH | 0 |
| Other C₈'s | 3 |
| TMP/DMH | 3.4 |

What is claimed is:

1. A process for transferring hydrogen from a paraffin to an olefin, said process comprising contacting said paraffin and said olefin under sufficient hydrogen transfer conditions, said paraffin and said olefin being contacted with a catalyst comprising MCM-36, said MCM-36 being a pillared, layered material having the X-ray diffraction pattern of Table 6.

2. A process according to claim 1, wherein the layers of the MCM-36 have a composition comprising the molar relationship $$X_2O_3:(n)YO_2,$$

wherein n is at least about 5, X is a trivalent element and Y is a tetravalent element, said MCM-36 having the X-ray diffraction pattern of Table 7.

3. A process according to claim 2, wherein X is selected from the group consisting of aluminum, boron, gallium and combinations thereof and Y is selected from the group consisting of silicon, germanium and combinations thereof.

4. A process according to claim 2, wherein X comprises aluminum and Y comprises silicon.

5. A process according to claim 1, wherein the paraffin contains from 4 to about 8 carbon atoms and the olefin contains from 2 to 12 carbon atoms.

6. A process according to claim 1, wherein the paraffin is isobutane.

7. A process according to claim 1, wherein the mole ratio of total isoparaffin to total olefin is from about 1:2 to about 500:1.

8. A process according to claim 1, wherein the mole ratio of total paraffin to total olefin is from about 5:1 to about 100:1.

9. A process according to claim 1, wherein the reaction temperature is from about −25° C. to about 400° C., the pressure is from below atmospheric to about 5000 psig and the weight hourly space velocity based on olefin is from about 0.01 to 100 hr 10. A process according to claim 1, wherein the reaction temperature is from about 75° C. to about 200° C., the pressure is from atmospheric to about 1000 psig and the weight hourly space velocity of the olefin is from about 0.05 to about 5 hr$^{-1}$.

11. A dual catalytic process for converting an isoparaffin feed and an olefin feed, said process comprising contacting both said isoparaffin feed and said olefin feed with a catalyst comprising MCM-36, said MCM-36 being a pillared, layered material having the X-ray diffraction pattern of Table 6, wherein the reaction conditions are sufficient to cause the following two results:
(i) the transfer of hydrogen, from said isoparaffin feed to said olefin feed, whereby isoparaffin feed is converted into olefin product and olefin feed is converted into a first paraffin product, said olefin product being different from said olefin feed; and
(ii) said olefin product from step (i) alkylates with unreacted isoparaffin in said isoparaffin feed to produce a second paraffin product having the number of carbon atoms equal to the sum of the carbon atoms in the olefin and isoparaffin which are reacted together in this step (ii).

12. A process according to claim 11, wherein said isoparaffin feed comprises a single isoparaffin compound.

13. A process according to claim 11, wherein said isoparaffin feed comprises more than one isoparaffin compound.

14. A process according to claim 11, wherein said olefin feed comprises a single olefin compound.

15. A process according to claim 11, wherein said olefin feed comprises more than one olefin compound.

16. A process according to claim 11, wherein said olefin feed comprises one or more olefins having from 6 to 12 carbon atoms.

17. A process according to claim 16, wherein said olefins of said olefin feed are branched olefins.

18. A process according to claim 11, wherein the layers of the MCM-36 have a composition comprising the molar relationship $$X_2O_3:(n)YO_2,$$

wherein n is at least about 5, X is a trivalent element and Y is a tetravalent element, said MGM-36 having the X-ray diffraction pattern of Table 7.

19. A process according to claim 18, wherein X is selected from the group consisting of aluminum, boron, gallium and combinations thereof and Y is selected from the group consisting of silicon, germanium and combinations thereof.

20. A process according to claim 18, wherein X comprises aluminum and Y comprises silicon.

21. A process according to claim 11, wherein the mole ratio of total isoparaffin to total olefin in the feed is from about 1:2 to about 500:1.

22. A process according to claim 11, wherein the reaction temperature is from about −25° C. to about 400° C., the pressure is from below atmospheric to about 5000 psig and the weight hourly space velocity based on olefin in the feed is from about 0.01 to 100 hr$^{-1}$.

23. A process according to claim 11, wherein the isoparaffin is isobutane and the olefin is 2,3-dimethyl-2-butene.

* * * * *